US011272999B2

(12) United States Patent
Ho et al.

(10) Patent No.: US 11,272,999 B2
(45) Date of Patent: Mar. 15, 2022

(54) DEVICES, SYSTEMS, AND METHODS TO SUPPORT, STABILIZE, AND POSITION A MEDICAL DEVICE

(71) Applicant: Evalve, Inc., Santa Clara, CA (US)

(72) Inventors: Patricia H. Ho, Redwood City, CA (US); Travis R. Marsot, Mountain View, CA (US); Christopher T. Strahm, Deforest, WI (US); Randall S. Koplin, Middleton, WI (US); Justen D. England, Milton, MA (US)

(73) Assignee: EVALVE, INC., Santa Clara, CA (US)

( * ) Notice: Subject to any disclaimer, the term of this patent is extended or adjusted under 35 U.S.C. 154(b) by 231 days.

(21) Appl. No.: 16/260,553

(22) Filed: Jan. 29, 2019

(65) Prior Publication Data

US 2019/0151041 A1 May 23, 2019

Related U.S. Application Data

(62) Division of application No. 14/879,674, filed on Oct. 9, 2015, now Pat. No. 10,226,309.

(51) Int. Cl.
*A61B 90/11* (2016.01)
*A61B 90/50* (2016.01)
*A61B 17/34* (2006.01)

(52) U.S. Cl.
CPC .............. *A61B 90/11* (2016.02); *A61B 90/50* (2016.02); *A61B 2017/3405* (2013.01); *A61B 2017/3407* (2013.01)

(58) Field of Classification Search
CPC ......... A61B 90/00; A61B 90/08; A61B 90/10; A61B 90/11; A61B 90/35; A61B 90/50;
(Continued)

(56) References Cited

U.S. PATENT DOCUMENTS

D406,337 S     3/1999  Baust et al.
D460,174 S     7/2002  Gallagher
(Continued)

FOREIGN PATENT DOCUMENTS

CN    103841899    6/2014
EP    1356773      10/2003
(Continued)

OTHER PUBLICATIONS

U.S. Appl. No. 14/879,674, dated May 15, 2018, Office Action.
(Continued)

*Primary Examiner* — Ahmed M Farah
(74) *Attorney, Agent, or Firm* — Workman Nydegger

(57) ABSTRACT

A stabilizer system for supporting a medical device includes a platform and a stabilizer body positioned on the platform and being slidably translatable about the platform. The platform includes a translation actuator configured to engage with a receiving member of the stabilizer body. Actuation of the translation actuator passes a force to the receiving member of the stabilizer body and causes the stabilizer body to translate relative to the platform. The stabilizer body includes a base and one or more support wings extending from the base to support a medical device. A straddle actuator is coupled to a support wing and is configured to engage with the medical device. Actuation of the straddle actuator passes a force to the medical device and causes at least a portion of the medical device to translate relative to the stabilizer body.

16 Claims, 9 Drawing Sheets

(58) Field of Classification Search
CPC .............. A61B 2090/508; A61B 17/34; A61B 2017/3405; A61B 17/3415; A61B 90/25; A61B 90/57; A61B 2017/3407
USPC ...................................................... 606/1, 130
See application file for complete search history.

(56) References Cited

U.S. PATENT DOCUMENTS

| | | | |
|---|---|---|---|
| D481,128 S | 10/2003 | Koros et al. | |
| D509,587 S | 9/2005 | McMinn et al. | |
| 7,666,204 B2 | 2/2010 | Thornton et al. | |
| 7,938,810 B2 | 5/2011 | Spranza et al. | |
| 8,079,444 B1 | 12/2011 | Rands et al. | |
| D666,711 S | 9/2012 | Baid | |
| 8,357,175 B2 | 1/2013 | Mark | |
| D702,833 S | 4/2014 | Cecchi | |
| 8,979,826 B2* | 3/2015 | Kappel | A61B 17/00234 606/1 |
| 8,986,246 B2* | 3/2015 | Foley | A61B 34/30 604/95.01 |
| 9,132,873 B1 | 9/2015 | Laurence et al. | |
| D750,224 S | 2/2016 | Miyano et al. | |
| D750,773 S | 3/2016 | Eaton et al. | |
| D762,300 S | 7/2016 | Breitweiser et al. | |
| 9,687,209 B2 | 6/2017 | Lee | |
| 9,782,224 B2 | 10/2017 | Piccin et al. | |
| D816,832 S | 5/2018 | Ho et al. | |
| 10,226,309 B2 | 3/2019 | Ho et al. | |
| 10,238,495 B2* | 3/2019 | Marsot | A61M 25/0136 |
| D847,983 S | 5/2019 | Ho et al. | |
| 10,820,954 B2* | 11/2020 | Marsot | A61B 34/70 |
| 2002/0151820 A1* | 10/2002 | Dvorak | A61B 90/17 600/562 |
| 2004/0049207 A1 | 3/2004 | Goldfarb et al. | |
| 2004/0054355 A1 | 3/2004 | Gerbi et al. | |
| 2007/0260225 A1 | 11/2007 | Sakakine et al. | |
| 2009/0247859 A1 | 10/2009 | Daum et al. | |
| 2010/0160825 A1 | 6/2010 | Parihar et al. | |
| 2012/0065464 A1 | 3/2012 | Ellis et al. | |
| 2012/0071895 A1* | 3/2012 | Stabler | A61B 6/12 606/130 |
| 2012/0182134 A1 | 7/2012 | Doyle | |
| 2012/0184955 A1 | 7/2012 | Pivotto et al. | |
| 2013/0190774 A1* | 7/2013 | Beira | A61B 34/72 606/130 |
| 2014/0236198 A1 | 8/2014 | Goldfarb et al. | |
| 2014/0316369 A1 | 10/2014 | Centeno et al. | |
| 2017/0042678 A1 | 2/2017 | Ganesan et al. | |

FOREIGN PATENT DOCUMENTS

| | | |
|---|---|---|
| JP | 2006528911 | 12/2006 |
| WO | WO 9309738 | 5/1993 |
| WO | WO 2014064694 | 5/2014 |

OTHER PUBLICATIONS

U.S. Appl. No. 14/879,674, Oct. 25, 2017, Office Action.
U.S. Appl. No. 14/879,674, May 15, 2018, Office Action.
U.S. Appl. No. 14/879,674, Oct. 30, 2018, Notice of Allowance.
U.S. Appl. No. 29/542,027, Dec. 29, 2017, Notice of Allowance.
U.S. Appl. No. 29/644,547, Dec. 10, 2018, Notice of Allowance.

* cited by examiner

DEVICES, SYSTEMS, AND METHODS TO SUPPORT, STABILIZE, AND POSITION A MEDICAL DEVICE

CROSS-REFERENCE TO RELATED APPLICATIONS

This application is a divisional of U.S. patent application Ser. No. 14/879,674, filed Oct. 9, 2015, now U.S. Pat. No. 10,226,309, the entire contents of which is incorporated herein by this reference.

BACKGROUND

The present disclosure relates generally to systems, devices, and methods for supporting, stabilizing, and/or positioning a medical device, such as a transcatheter medical device.

Various medical procedures require the controlled use of medical devices. Typically, during such a medical procedure, a portion of a medical device must be positioned near a patient's body or near a surgical site during the medical procedure. Often, during such procedures, the medical device must be manipulated and repositioned, and in many instances one portion of the medical device must be moved relative to another portion of the medical device. On the other hand, inadvertent movement or unintended positioning of the medical device during a delicate medical procedure is undesirable and can be dangerous to the patient, particularly when there are portions of the medical device, such as a catheter or implant, that have been positioned within the body.

A medical device can be positioned on a stabilizer to hold it in place relative to a patient or surgical site and to reduce the risk of inadvertent movement of the medical device. However, when adjustment or repositioning of the medical device is required, the entire stabilizer must typically be picked up and repositioned, thereby reintroducing the very risks the stabilizer was intended to limit. In addition, movement of one portion of the medical device relative to another portion may be constrained by the stabilizer, requiring a surgeon or other user to de-couple the medical device or a portion of it from the stabilizer in order to make the desired adjustments. Such decoupling reduces the desired stability intended by use of the stabilizer.

BRIEF SUMMARY

Embodiments of the present disclosure are directed toward stabilizer systems for supporting a medical device. Certain embodiments include a platform; a translation actuator coupled to the platform; and a stabilizer body positioned on the platform and being translatable about the platform, the stabilizer body including a receiving member configured to engage with the translation actuator; wherein actuation of the translation actuator passes a force to the receiving member allowing the stabilizer body to translate relative to the platform.

Certain embodiments are directed toward a stabilizer system for supporting a medical device, including a medical device including a receiving element; a stabilizer body including a base and one or more support wings extending from the base, the medical device being supported by the one or more support wings and being translatable about at least one of the one or more support wings; and a straddle actuator coupled to the one or more support wings and configured to engage with the receiving element; wherein actuation of the straddle actuator passes a force to the receiving element allowing at least a portion of the medical device to be translated relative to the stabilizer body.

Certain embodiments are directed toward a method for positioning a medical device, the method including positioning a medical device upon a stabilizer body, the stabilizer body being positioned upon a platform and including a receiving member, the platform including a translating actuator configured to engage with the receiving member and to pass a force to the receiving member upon actuation of the receiving member; and translating the stabilizer body relative to the platform by actuating the translation actuator.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. Embodiments of the disclosure will be described and explained with additional specificity and detail through the use of the accompanying drawings in which.

DETAILED DESCRIPTION

The present disclosure relates to devices, systems, and methods for supporting, stabilizing, and positioning a medical device. Certain embodiments can advantageously allow adjustment and/or positioning of a medical device while maintaining stable support of the medical device upon the stabilizer. At least one embodiment may allow adjustment and/or positioning of a medical device without requiring movement of the entire stabilizer system. In addition, certain embodiments can advantageously allow a portion of a medical device to be manipulated and/or repositioned relative to another portion of a medical device, where at least one embodiment does not require decoupling of the medical device from the stabilizer. Further, certain embodiments can advantageously hold and/or lock a medical device or a portion thereof in a desired position while preventing unintended and undesirable movement of the medical device.

Figure 1:
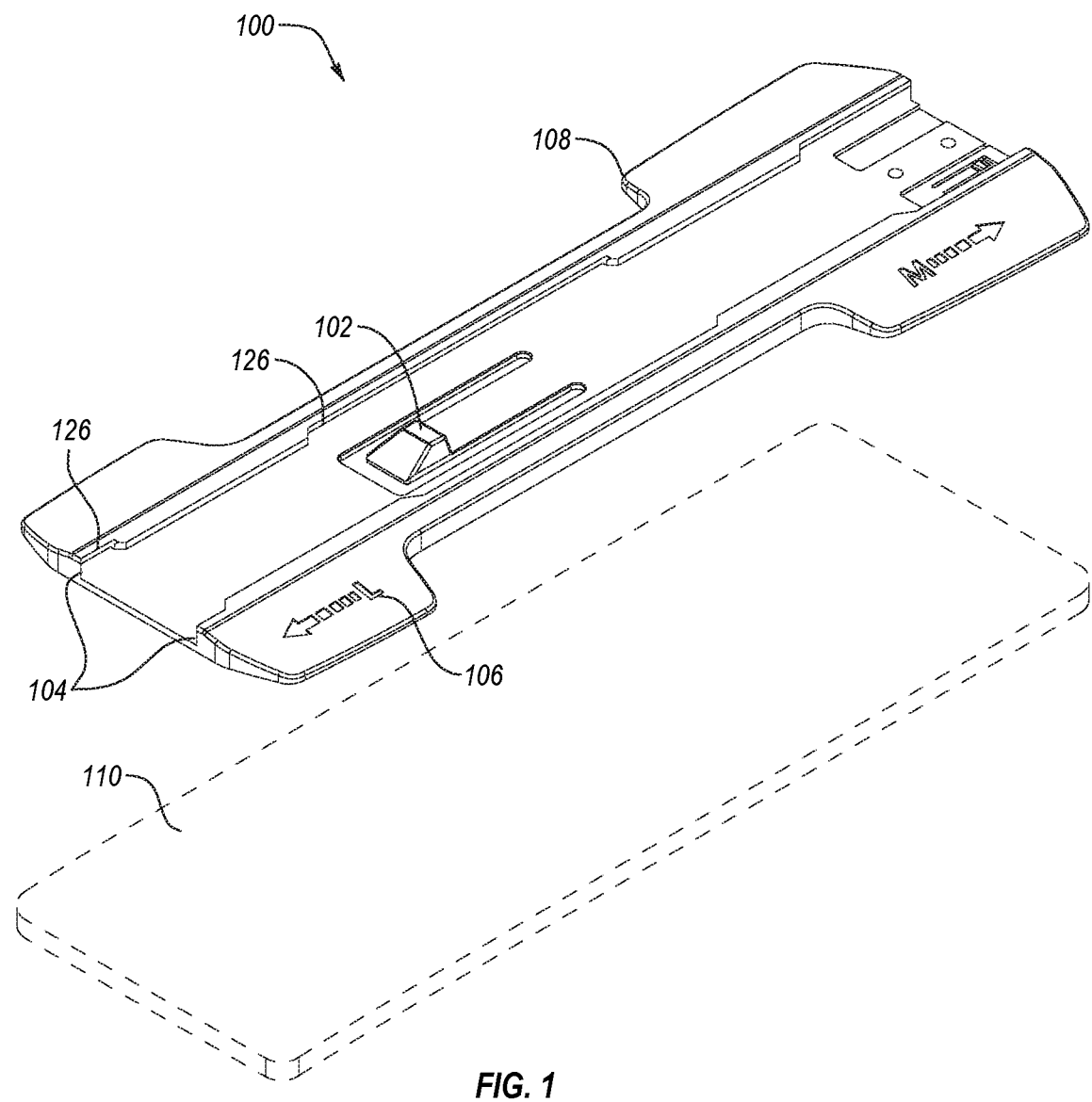
FIG. 1 illustrates an embodiment of a platform.

FIG. 1 illustrates one embodiment of a platform 100 for supporting a stabilizer system according to the present disclosure. The illustrated platform 100 includes a stop 102. In this embodiment, the stop 102 is configured as a raised tab. As explained in more detail below, the stop 102 is configured to limit translation of a stabilizer body beyond the stop 102. Other embodiments may omit stops, and yet other embodiments may include additional stops (e.g., oppositely disposed stops configured to limit translation in two directions along the platform).

The illustrated platform 100 may include a pair of oppositely disposed insertion grooves 104. The insertion grooves 104 are formed so as to allow the insertion of a stabilizer body within the insertion grooves 104 and/or to provide a resilient structure for holding a stabilizer body in place upon the platform 100. Additionally, or alternatively, some embodiments may include other means of holding the stabilizer body in position. For example, some embodiments may include one or more tabs, clamps, clips, channels, grooves, pins, or other structures for holding and/or supporting a stabilizer body positioned upon the platform. As illustrated, in some embodiments the insertion grooves include one or more insertion groove cutouts 126. As described in more detail below, the one or more insertion groove cutouts 126 can be configured to hold a stabilizer body in position upon the platform 100 until the stabilizer body is aligned with the insertion groove cutouts 126. Upon alignment, the stabilizer body can be lifted away from the platform 100.

The platform 100 may be formed from a variety of materials, including plastics and other polymers (e.g., polyesters, polyethylenes, polyvinyl chlorides, polypropylenes, polystyrenes, polyamides, polycarbonates, polyurethanes), metals (e.g., stainless steel), ceramics, and the like. In some embodiments, the platform 100 can be formed from a polyoxymethylene, such as the material sold under the name Delrin®. In some embodiments, a pad 110 (e.g., formed from rubber, silicone) may be attached to the underside of the platform 100 to provide additional anti-slippage and/or to improve positioning of the platform 100. In some embodiments, the platform 100 may include one or more overmolded components (e.g., pad 110 may be overmolded to at least a portion of the platform 100).

The illustrated platform 100 may include direction indicators 106. Direction indicators 106 can aid a user in orienting the platform, such as during surgery preparation, and/or can be used to indicate a position of movement and/or translation (e.g., medial/lateral, anterior/posterior) of the stabilizer and/or medical device during a medical procedure, for example. The illustrated platform 100 may include a plurality of flared portions 108. Such flared portions 108 can aid in the gripping and/or handling of the platform 100. In addition, the flared portions 108 can provide the needed surface area for positioning and maintaining the platform 100 at a desired location without tipping and/or sliding (e.g., on a desired surface during a medical procedure).

Figure 2:
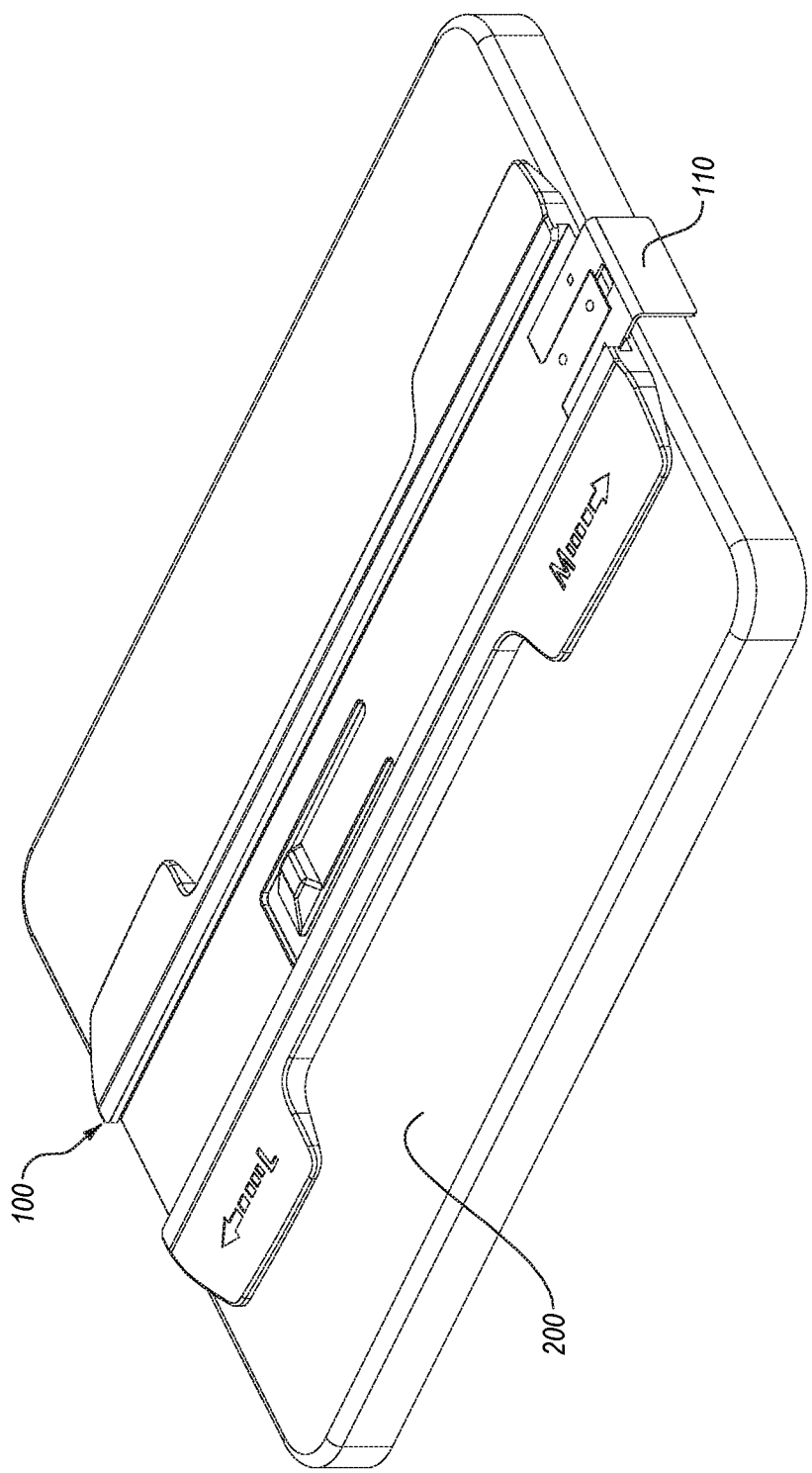
FIG. 2 illustrates an embodiment of a platform positioned upon a surface.

FIG. 2 illustrates an embodiment of a platform 100 positioned on a surface 200. The surface 200 can be, for example, the surface of a stool, bench, tabletop, or other suitable surface suitable for use in a medical procedure and/or in medical or lab testing. In some embodiments, additional materials may be placed between the surface 200 and the platform 100 in order to aid in maintaining the position of the platform 100 upon the surface 200. For example, silicone padding, adhesives, and/or hook and loop fasteners (e.g., Velcro®) may be used in the placement of the platform 100 upon the surface 200.

The illustrated embodiment includes a stop plate 110 coupled to one end of the platform 100 and extending around an edge of the surface 200. The illustrated stop plate 110 is configured in size and shape to fold around an edge of the surface 200 to prevent the platform 100 from moving away from the edge of the surface 200. Other embodiments may include additional stop plates. For example, some embodiments may include a pair of oppositely disposed stop plates, with one disposed on a first end of the platform and another disposed on an opposite end, the stop plates thereby preventing the platform from moving away from either of two oppositely disposed edges of the surface 200. Additionally, or alternatively, separate structures may be used to prevent and/or limit movement of the platform 100 upon the surface 200. For example, one or more hooks, clamps, clasps, pins, ties, tabs, and/or other fasteners may be used.

Figure 3:
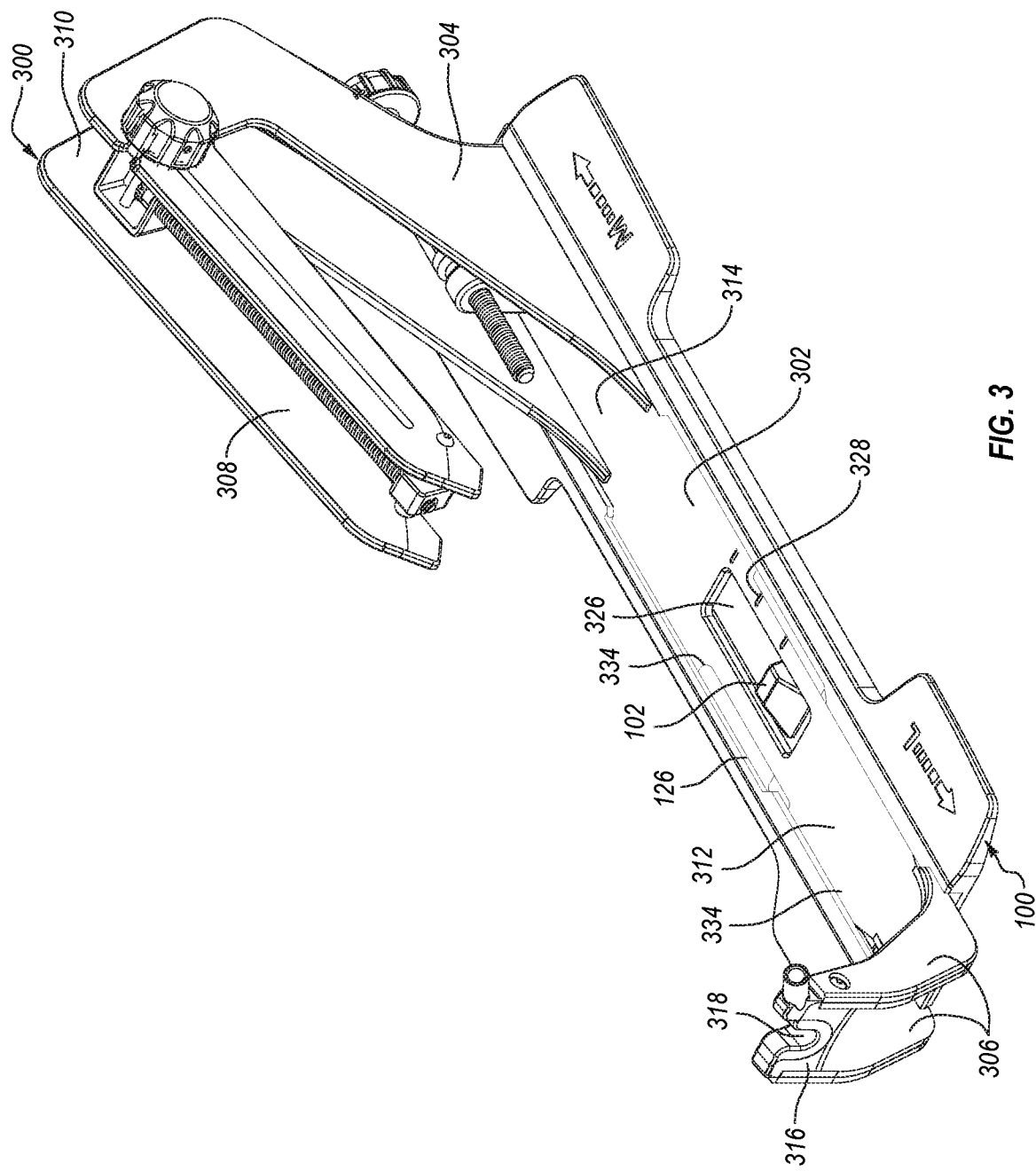
FIG. 3 illustrates an embodiment of a stabilizer body positioned upon a platform.

FIG. 3 illustrates an embodiment of a stabilizer body 300 positioned upon a platform 100. The stabilizer body 300 of the illustrated embodiment is inserted into the insertion grooves 104 of the platform 100 and is configured so as to be translatable on the platform along an axis of the insertion grooves 104. In some embodiments, the stabilizer body 300 and platform 100 are configured to allow attachment and detachment of the stabilizer body 300 and the platform 100 by translating (e.g., horizontally sliding) the stabilizer body 300 into the insertion grooves 104. Additionally, or alternatively, the stabilizer body 300 and the platform 100 can be attached and/or detached by vertically moving the stabilizer body 300 relative to the platform 100. For example, the illustrated platform 100 includes insertion groove cutouts 126, and stabilizer body 300 includes insertion tabs 334. The insertion tabs 334 can be inserted into the insertion grooves 104 of the platform so as to translatably secure the stabilizer body 300 within the platform 100. The stabilizer body 300 can be selectively translated to bring the insertion tabs 334 into alignment with the insertion groove cutouts 126 (e.g., by translating the stabilizer body 300 forward until hitting the stop 102). In the aligned position, the stabilizer body 300 may be lifted up and away from the platform 100.

The illustrated stabilizer body 300 also includes a stop window 326 positioned to allow the stop 102 of the platform 100 to pass through the stop window 326. In this configuration, the stop 102 can limit the translation of the stabilizer body 300 by abutting against an edge of the stop window 326 and preventing further translation of the stabilizer body. The illustrated stabilizer body 300 may include position indicators 328 disposed near the stop window 326. In this embodiment, a user can measure the relative positions of the platform 100 and stabilizer body 300 by gauging the alignment of the stop 102 relative to the position indicators 328.

The size of the platform 100 relative to the stabilizer body 300 can vary. For example, in the illustrated embodiment, the platform 100 has a length that is equal to or about equal to the length of the base 302 of the stabilizer body 300. In other embodiments, the platform and/or stabilizer body 300 can be differently sized. For example, some embodiments may include a platform having a shorter or longer length than the length of the base of the stabilizer body. Additionally, or alternatively, some embodiments may include a platform that is offset from the base; for example, offset a distance forward or rearward. For example, in the illustrated embodiment, the base 302 of the stabilizer body 300 can be centered on the platform 100 within the range of translation of the stabilizer body 300 (e.g., centered on the platform 100 when the stabilizer body 300 is positioned in a rearward-most position). However, in other embodiments, a base of a stabilizer body can be offset from a platform such that the base is not centered on the platform within the range of translation of the stabilizer body upon the platform.

The stabilizer body 300 illustrated in FIG. 3 includes a base 302 and a pair of rear support wings 304 extending from a rear portion 314 of the base 302, and a pair of front support wings 306 extending from a front portion 312 of the base 302. Other embodiments may omit one or more support wings, may include additional support wings, and/or may include one or more support wings having a different configuration. For example, some embodiments may include a single or solid front support wing and/or rear support wing, as opposed to the bifurcated adjacent pair of rear support wings 304 and/or front support wings 306 illustrated in FIG. 3.

The illustrated stabilizer body 300 may include a pair of cross members 308. Each cross member 308 may extend from one of the rear support wings 304 toward the front support wings 306, as shown. In the illustrated embodiment, the pair of cross members 308 are integrally joined to the pair of rear support wings 304, forming a pair of adjacent plate structures extending from the base 302 and formed in the shape of the rear support wings 304 and the cross members 308. The adjacent cross members 308 of the illustrated embodiment may define a straddle area 310 located between the adjacent cross members 308. In another example, the straddle area 310 may be disposed between adjacent rear support wings 304 and/or adjacent cross members 308.

In other embodiments, one or more cross members 308 may be separately joined to a rear support wing 304. Other embodiments may also include a different number of cross members 308 and/or may include one or more cross members 308 of a different size and/or configuration. For example, some embodiments may include one or more cross members that extend from a rear support wing in a rearward direction (e.g., as an alternative to, or in addition to, extending from a rear support wing in a forward direction). Some embodiments may include a single cross member extending from a rear support wing, with a straddle area being formed as a bend, channel, groove, or the like in the single cross member.

Some embodiments may include more than two cross members extending from support wings and may include more than one straddle area disposed between adjacent cross members. Some embodiments may omit cross members and/or may include one or more rear support wings having a length along a top section that functions as a cross member. In addition, some embodiments may include one or more cross members having slotted portions, such as a longitudinally running slotted portion for the sliding and positioning of additional components disposed within a straddle area.

In the illustrated embodiment, the pair of rear support wings 304 are angled away from the base 302 in a rearward and upward direction, and the pair of front support wings 306 are angled away from the base 302 in a frontward and upward direction. In addition, the pair of front support wings 306 extend a shorter distance upward, relative to the base 302, than the pair of rear support wings 304. In this configuration, the cross members 308 and the front support wings 306 create an angled plane (i.e., angled relative to the base 302) for supporting and stabilizing a medical device positioned thereon.

In other embodiments, various support wings and/or cross members may have different shapes and/or extension angles, and may form a differently angled plane for supporting a medical device. For example, in some embodiments, one or more front support wings may extend to a greater height from the base than the rear support wing(s), or may extend to the same height from the base as the rear support wing(s). In some embodiments, one or more of the front and/or rear support wings may be angled away from the base differently than in the illustrated embodiment. For example, in some embodiments, one or more front and/or rear support wings may extend substantially perpendicular from the base of the stabilizer body, or one or more front support wings may extend at a rearward angle from the base, and/or one or more rear support wings may extend at a frontward angle from the base.

The illustrated embodiment of the stabilizer body 300 also includes a support block 316 disposed between the pair of front support wings 306. The support block 316 is configured to support and hold a portion of a medical device positioned upon the stabilizer body 300. In this embodiment, the support block 316 includes a notch 318 for receiving the portion of the medical device to be supported by the front support wings 306 of the stabilizer body 300.

In other embodiments, the support block 316 may be omitted, may be differently sized and/or configured, or may be integrally formed with the front support wings. For example, in some embodiments, one or more front support wings may be configured to engage with and support the portion of the medical device positioned above the front support wing(s) without any support block. In some embodiments, the support block and/or one or more support wings may include additional notches and/or may include other structures for supporting and securing a portion of a medical device in position. For example, some embodiments may include one or more grooves, channels, guides, apertures, collets, clamping sections, or the like, or combinations thereof. In some embodiments, as explained in more detail below, the support block 316 may be configured to provide frictional locking of the medical device or portion thereof held by the support block 316, preventing inadvertent movement while still allowing for intentional manipulation and adjustment of the medical device. For example, the support block 316 may prevent rotation (and/or translation) by, for example, friction. Additionally, or alternatively, the support block 316 may be configured to receive a support pin (e.g., a set screw and/or spring pin) for supporting and/or fastening a medical device or a portion thereof.

In some embodiments, the angle of the platform 100 relative to the stabilizer body 300 can vary. For example, in some embodiments, the platform 100 can be angled to be higher at a rear section and lower at a front section. In some embodiments, the stabilizer body 300 and/or the platform 100 can be configured to provide a desired angle of an attached medical device.

Figure 4:
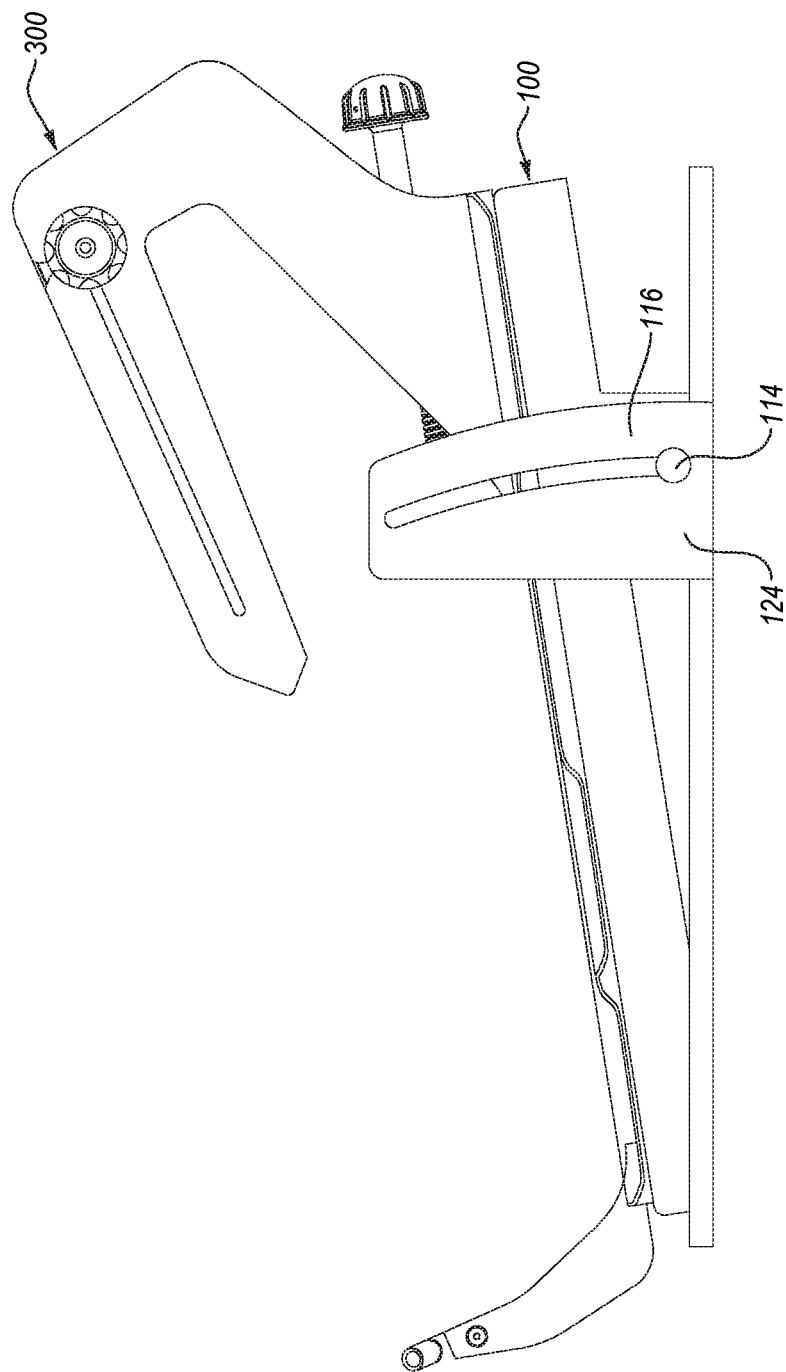
FIG. 4 illustrates an embodiment of a stabilizer body positioned upon a height-adjustable platform.

FIG. 4 illustrates an embodiment of a platform 100 having a height-adjustable configuration. As illustrated, a stabilizer body 300 may be positioned on the platform 100. The height and/or angle of the stabilizer body 300 can be adjusted by manipulating an adjustment component 124. As shown, the adjustment component 124 can include a slide 116 configured to receive a pin 114. Movement of the pin 114 within the slide 116 can cause the rest of the platform 100 to be raised or lowered. Accordingly, raising or lowering the platform 100 can cause the angle and/or height of the stabilizer body 300 to be raised or lowered. In the illustrated embodiment, the adjustment component 124 is disposed near a rear section of the stabilizer body 300 (e.g., when the stabilizer body 300 is positioned upon the platform 100). In other embodiments, the adjustment component 124 may be disposed closer to a front section of the stabilizer body 300, or at or near a mid-section of the stabilizer body 300.

The position of the adjustment component 124 can be selected to provide a desired range of angular adjustment to a stabilizer body 300 positioned upon the platform 100. For example, the position and/or length of the slide 116 can be configured to provide a desired range of angular adjustment, such that a medical device coupled to the stabilizer body 300 can be positioned at a desired angle within the range of angular adjustment.

Figure 5:
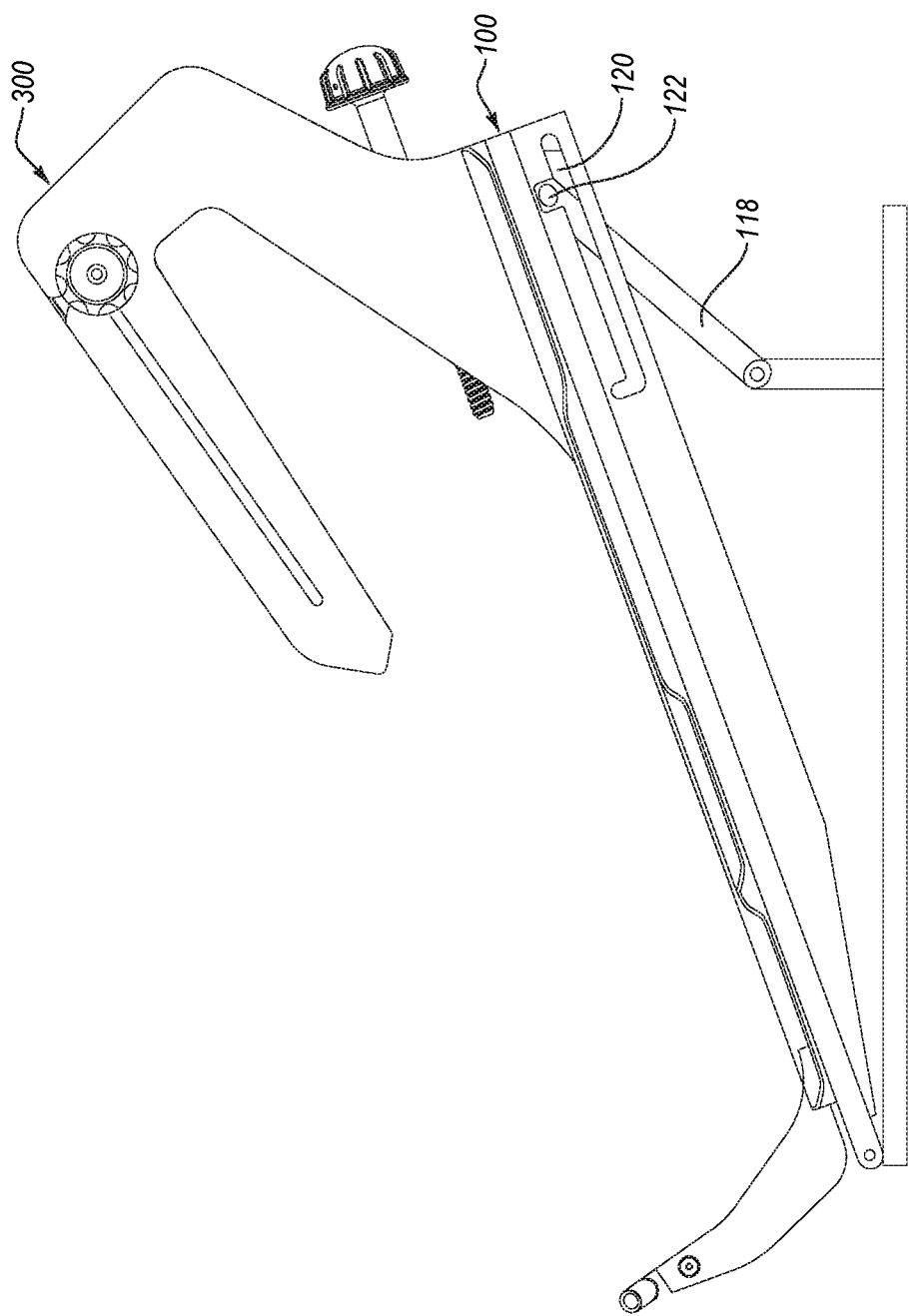
FIG. 5 illustrates another embodiment of a height-adjustable platform.

FIG. 5 illustrates another embodiment of a platform 100 having a height-adjustable configuration. As illustrated, the platform 100 can be configured to support a stabilizer body 300. The platform 100 can include an adjustment component 118. In the illustrated embodiment, the adjustment component 118 is formed as a pivotable support having a pin 122 that may be inserted into a slot 120 of the platform 100. The slot 120 may include one or more notches configured to receive the pin 122 in order to secure the position of the platform 100.

The embodiments illustrated in FIGS. 4 and 5 are merely examples of height-adjustable platforms. Other embodiments can include different height-adjusting means in addition to, or alternative to, the illustrated embodiments. For example, some embodiments may include one or more hinges configured to provide height adjustment to the platform, and one or more pins, braces, posts, stops, detents, or other securing means for holding the platform at a desired angle. In some embodiments, friction between adjustable components may be enough to secure the platform to a desired angle and/or height. In some embodiments, one or more threaded components may be positioned between adjustable portions of the platform, and adjustment of the height and/or angle of the platform can be accomplished by turning or otherwise manipulating the threaded component.

Figure 6:
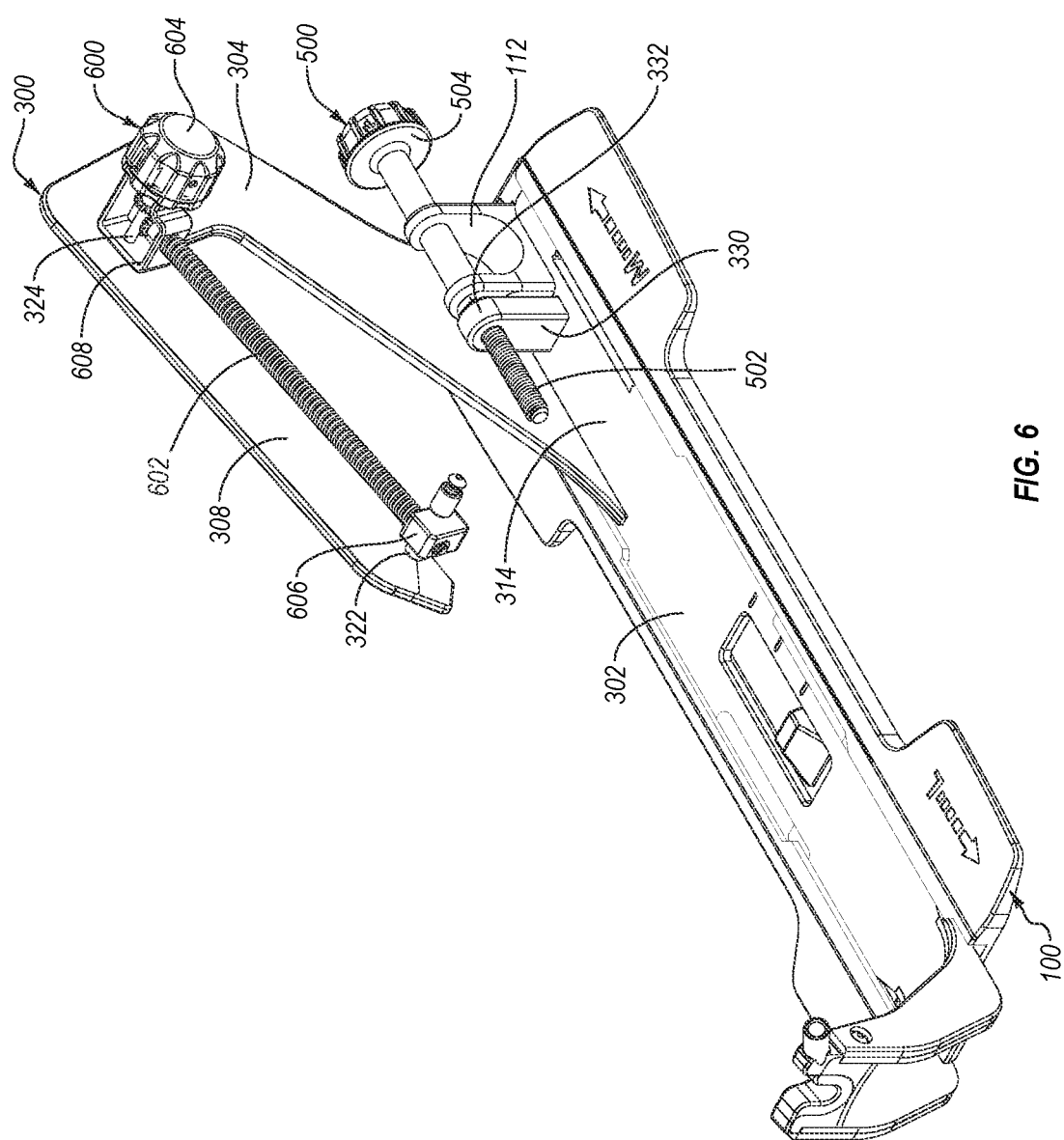
FIG. 6 illustrates a partial cutaway of the embodiment shown in FIG. 3 to show a translation actuator and a straddle actuator.

FIG. 6 illustrates the embodiment of a stabilizer body 300 and the embodiment of the platform 100 shown in FIG. 3, with a rear support wing 304 removed to better show additional elements of the stabilizer system. As shown, the illustrated stabilizer body 300 includes a receiving member 330 extending from the base 302 and disposed between the pair of rear support wings 304. A translation actuator 500 may be disposed near the rear portion 314 of the stabilizer body 300 and/or may be coupled to the platform 100 by passing through a bearing block 112. The bearing block 112 may extend from the platform 100 to a sufficient height or a height that is substantially equal to the height of the receiving member 330 when the stabilizer body 300 is positioned upon the platform. The illustrated bearing block 112 includes an arcuate cutout, reducing the surface area of the bearing block 112 and providing access to the remaining surfaces. Such an embodiment can beneficially provide for easier cleaning of the bearing block 112 and surrounding surfaces (e.g., by enabling easier application of antiseptics to inner surfaces of the bearing block 112, easier scrubbing, etc.).

In some embodiments, the bearing block 112 can be formed as a threaded member configured to receive matching threads of a translation leadscrew 502. In other embodiments, the bearing block and/or portions of the translation actuator can be configured as other means of transmitting a translation force. For example, a bearing block may be configured as a split nut allowing a user to disengage threads (e.g., in order to quickly remove a translation leadscrew). In some embodiments, a bearing block may be formed as a hinged element configured to be opened to release a translation leadscrew (or other translation force means).

The illustrated translation actuator 500 may be configured to engage with the receiving member 330 and/or may be configured to transmit a force to the receiving member 330 upon actuation of the translation actuator 500. In the illustrated embodiment, the translation actuator 500 includes a translation knob 504 coupled to a translation leadscrew 502, and the receiving member 330 includes a nut 332 configured to receive and engage the translation leadscrew 502. In this embodiment, rotation of the translation knob 504 causes rotation of the translation leadscrew 502, and rotation of the translation leadscrew 502 passes a force to the nut 332 (e.g., via contact between outer threads of the translation leadscrew 502 and inner threads of the nut 332), causing the stabilizer body 300 to translate along the platform 100. In other embodiments, the translation actuator 500 may include a sliding mechanism with detents, a sprocket and chain assembly, a gear and gear rack assembly, a push and/or pull rod assembly, or combinations thereof, for example.

In other embodiments, a translation actuator and/or a receiving member can be positioned in different locations and/or can be formed with alternative configurations. For example, in some embodiments, a receiving member can be positioned rearward relative to a bearing block and/or can be joined to one or more separate components of the stabilizer body (e.g., to one or more support arms). In some embodiments, the translation actuator and/or receiving member can include and/or be formed from different components. For example, some embodiments may include a translation actuator coupled to a receiving member through a chain and sprocket assembly, belt and pulley assembly, gear and gear rack assembly, a sliding mechanism (e.g., with detents), or other structures and assemblies configured to allow the transmission of force from the translation actuator to the receiving member.

In the illustrated embodiment, the translation knob 504 is positioned near the rear portion 314 of the stabilizer body 300 and to the rear of the bearing block 112 and the receiving member 330. In other embodiments, the knob 504 may be positioned in a different location and/or may be differently configured in size and/or shape. For example, in some embodiments, a knob may be positioned in front of the bearing block 112 and the receiving member 330, or may be positioned in between the bearing block 112 and the receiving member 330.

In the illustrated embodiment, the translation knob 504 is coaxially aligned with the translation leadscrew 502. In other embodiments, the translation knob 504 can be offset from a longitudinal axis of the translation leadscrew 502 (e.g., by using miter gears, differentials, cranks, or other angled force transmission means).

In addition to, or alternative to, the translation knob 504, some embodiments can include a translation actuator having one or more handles, control rods, levers, slides, dials, or other means of transmitting a force (e.g., rotational or linear) from the translation actuator to the receiving member.

The translation actuator 500 and the receiving member 330 can be configured to allow the stabilizer body 300 to be translated along the platform 100 through a span ranging from 1 to 25 cm, or from 2 to 20 cm, or from 3 to 15 cm, or from 4 to 10 cm, or from 5 to 8 cm.

FIG. 6 also illustrates a straddle actuator 600 coupled to the cross member 308. In this embodiment, the straddle actuator 600 is aligned with the cross member 308 and is sized to run across the length of the cross member 308 (e.g., across 30% or more of the length of the cross member 308, or across 40%, 50%, 60%, 70%, 80%, 90%, or 100% of the length of the cross member 308).

As illustrated in FIG. 6, the straddle actuator 600 can be disposed in the straddle area 310 between adjacent cross members 308. The illustrated straddle actuator 600 is positioned in the straddle area 310 by being coupled to a forward pin 322 and a rearward pin 324, the forward pin 322 and the rearward pin 324 spanning across or into the straddle area 310 to provide a support structure to which the straddle actuator 600 can be positioned. In other embodiments, the straddle actuator 600 can be coupled to the stabilizer body 300 at other locations and/or in other ways (e.g., may be welded in place). For example, in some embodiments, a straddle actuator can be positioned above or to a side (e.g., an outer side) of a cross member, or can be positioned above or to a side of a rear support wing (e.g., in embodiments that omit cross members).

The illustrated straddle actuator 600 includes a straddle leadscrew 602 disposed between a forward block 606 and a gear box 608, with a straddle knob 604 coupled to the gear box 608. The forward block 606 can be configured to be coupled to and/or supported by the forward pin 322 and the gear box 608 can be configured to be coupled to and/or supported by the rearward pin 324. The gear box 608 may include a gear assembly configured to allow the straddle knob 604 to be angled away from the longitudinal axis of the straddle leadscrew 602. Referring back to FIG. 3, the straddle knob can pass through one of the rear support wings 304 (e.g., through a notch as shown, or through an aperture, slot, or other suitable passage) to couple with the gear box 608.

Other embodiments can include a straddle actuator located at a different position on a stabilizer body and/or a differently configured straddle actuator. For example, some embodiments can include a straddle knob that is offset from a longitudinal axis of a straddle leadscrew on an opposite side (e.g., relative to the embodiment shown in FIG. 3) or offset above or below a straddle leadscrew. The straddle actuator can include a straddle knob that is coaxially aligned with the longitudinal axis of a straddle leadscrew, thereby eliminating the need for gears.

In addition to, or alternative to, the straddle knob 604, some embodiments can include a straddle actuator having one or more handles, control rods, levers, slides, dials, other means of actuating a force (e.g., rotational or linear), or combinations thereof in the straddle actuator. Further, some embodiments can include a straddle knob or other such actuating means disposed at the front or mid-section of a straddle actuator.

The straddle actuator 600 and the translation actuator 500 illustrated in FIG. 6 can be removed from the stabilizer body 300 and/or platform 100. This may advantageously provide for easier cleaning and/or sterilization of the separated parts. Under some circumstances, however, the straddle actuator 600 and the translation actuator 500 can remain coupled to the stabilizer body 300 and/or platform 100 during cleaning and/or sterilization, as the resulting assembly may advantageously omit hidden edges and/or can also be easily cleaned and sterilized in an assembled configuration.

Figure 7:
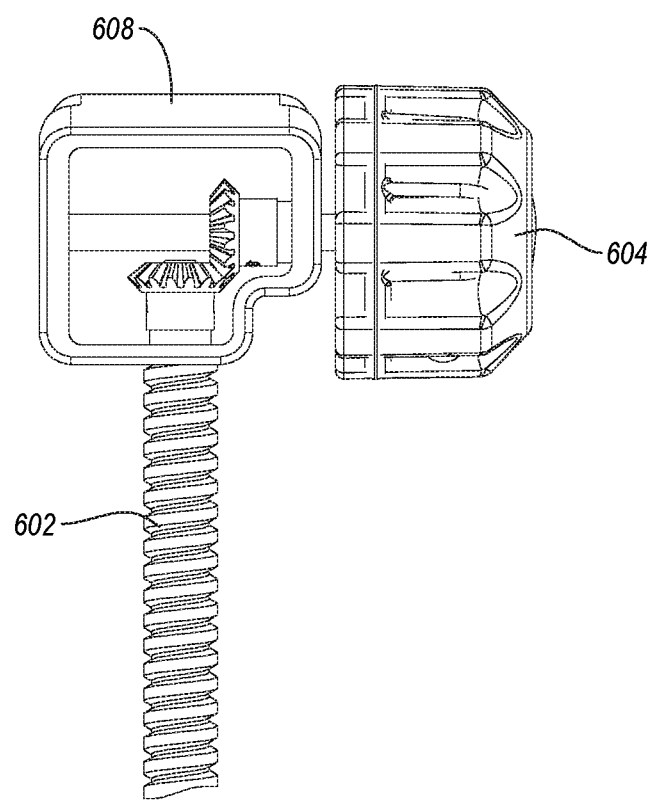
FIG. 7 illustrates an embodiment of a gear box assembly of the straddle actuator shown in FIG. 4.

FIG. 7 illustrates the embodiment of the straddle leadscrew 602, straddle knob 604, and gear box 608 shown in FIGS. 3 and 6. As illustrated, the gear box 608 can include a pair of miter gears configured to offset the straddle knob 604 by 90 degrees from the straddle leadscrew 602. In other embodiments, a gearbox can be configured to offset a straddle knob by a smaller or larger angle (e.g., 30, 60, 120, or 150 degrees) from a straddle leadscrew. As illustrated, the straddle knob 604 can have a plurality of fins 610 arrayed along the outer surface of the straddle knob 604 in order to provide a gripping surface for actuating the straddle knob 604. Other embodiments may omit fins 610 and/or may include other structures, such as grooves, ridges, bumps, or other features to provide easier gripping and/or ergonomic actuation of the straddle knob. In some embodiments, straddle actuator 600 and/or other portions of the device can include instructive labeling. For example, a label can indicate to a user the relationship between actuation of a knob (e.g., straddle knob 604) and the distance the medical device is moved (e.g., one turn of knob is about 2 cm of translation).

Figure 8:
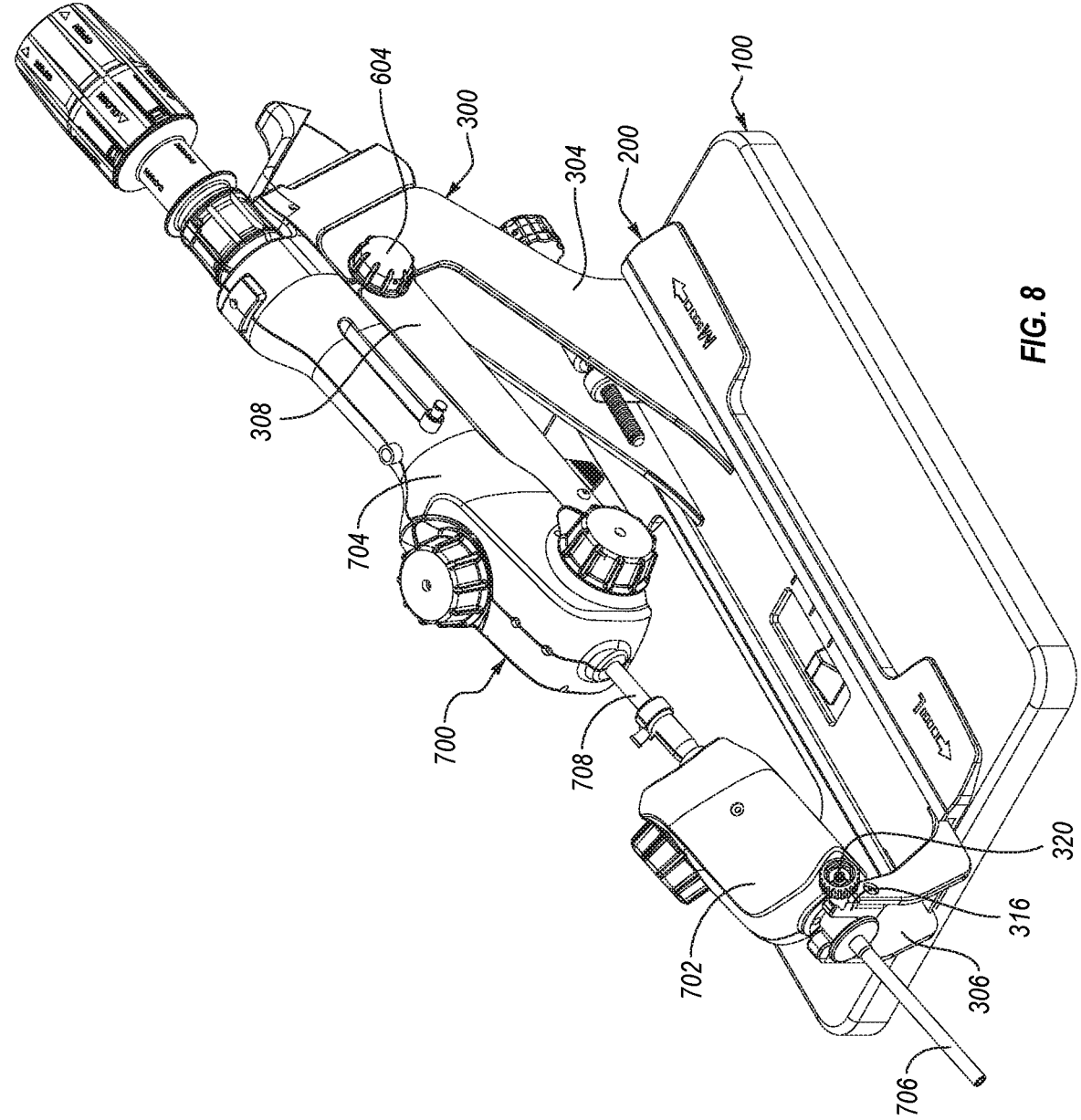
FIG. 8 illustrates an embodiment of a medical device positioned upon a stabilizer body.

FIG. 8 illustrates an embodiment of a stabilizer body 300 positioned upon a platform 100, with a medical device 700 being supported by the stabilizer body 300. Examples of a medical device 700 may be found in U.S. patent application Ser. No. 14/879,726, filed Oct. 9, 2015. As illustrated, the stabilizer body 300 can be configured such that the front support wings 306 and/or support block 316 support a first portion 702 of the medical device 700 and the rear support wings 304 and/or cross members 308 support a second portion 704 of the medical device 700. The second portion 704 can be configured to engage with the cross members 308 so as to be slidably coupled to the cross members 308.

As illustrated, the first portion 702 can be held in position by the support block 316. In this embodiment, a support pin 320 can be included, the support pin 320 being configured to provide a resilient force against the first portion 702 supported by the support block 316 (e.g., as a spring pin, set screw, friction rod, dowel, etc.). In such embodiments, the support block 316 can function as a frictional lock, allowing the first portion 702 to maintain a second orientation after being reoriented from a first orientation. For example, the support pin 320 can function to prevent rotation (and/or translation) of the first portion 702 until sufficient force is applied (e.g., from a user's hand) to overcome the resilient biasing of the support pin 320 to allow reorientation of the first portion 702.

As illustrated, the second portion 704 can be translated along the cross members 308 by actuating the straddle actuator 600 (e.g., by actuating straddle knob 604). In this embodiment, the second portion 704 is translatable relative to the first portion 702. For example, the medical device 700 may include an outer catheter 706 coupled to the first portion 702 and/or an inner sleeve 708 coupled to the second portion 704. The inner sleeve 708 may be translatable within the outer catheter 706 by translating the second portion 704 relative to the first portion 702.

In other embodiments, one or more different components may be coupled to a first and/or second portion of a medical device. For example, an introducer, sleeve, or other lumen or guide may be coupled to the first portion while a catheter, lumen, guidewire, or delivery device may be coupled to the second portion.

Some embodiments may include a medical device that is not formed with two separate portions. For example, some embodiments may include a stabilizer body that does not lock or prevent translation of any portion of a supported medical device, such that the entire medical device may be translated relative to the stabilizer body upon actuation of the straddle actuator.

Figure 9:
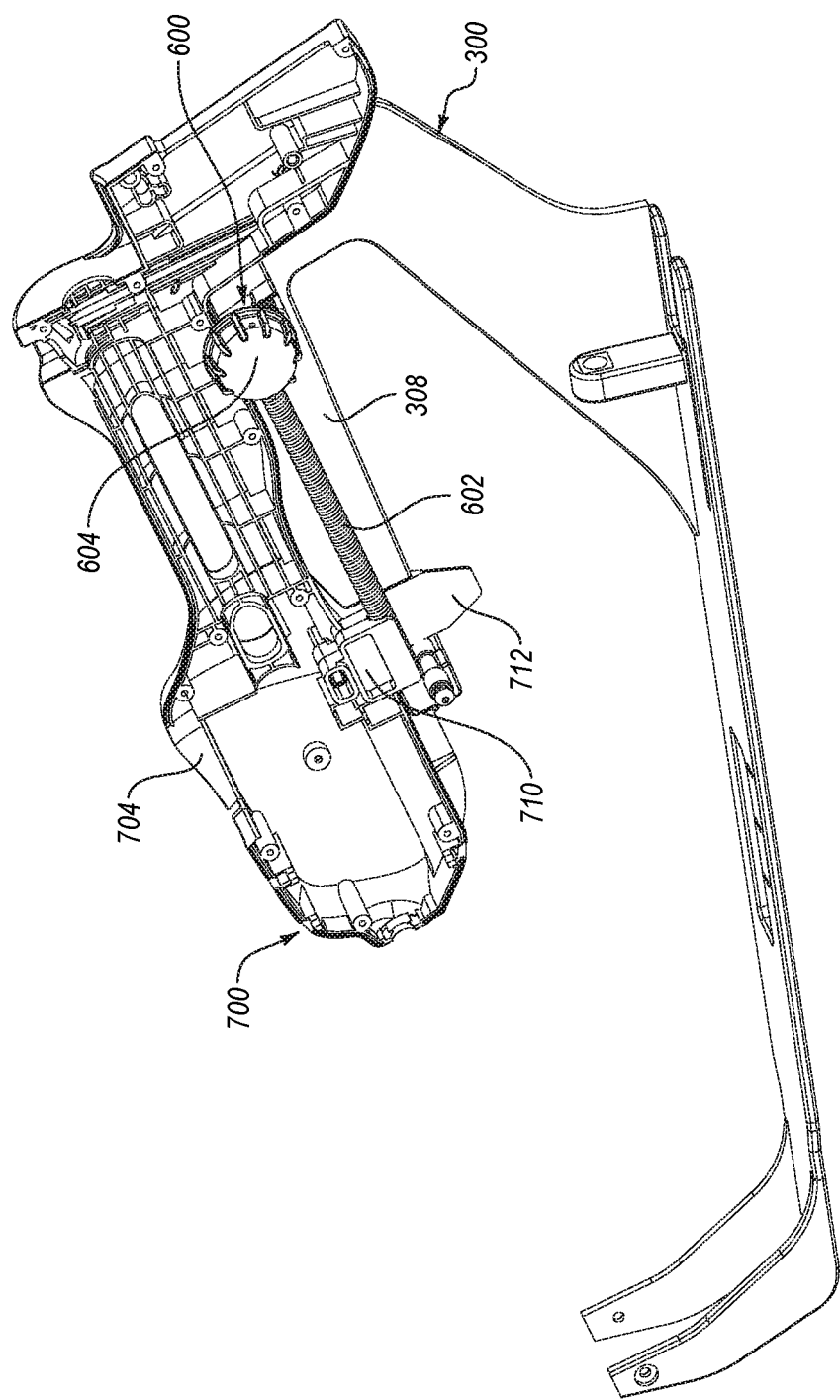
FIG. 9 illustrates a partial cutaway of the embodiment shown in FIG. 6 to show the relationship between a straddle actuator and a medical device.

FIG. 9 illustrates a partial cutaway of a second portion 704 of a medical device 700 supported by a stabilizer body 300. In the illustrated embodiment, some components of the stabilizer body 300 have been removed to better show the relationship between the straddle actuator 600 and the second portion 704. As shown, the second portion 704 can include a receiving element 710 configured to engage with the straddle actuator 600. In this embodiment, the straddle actuator includes a straddle leadscrew 602, and the receiving element 710 is configured to be positioned upon the straddle leadscrew 602 such that rotation of the straddle leadscrew 602 causes outer threads of the straddle leadscrew 602 to engage with inner threads of the receiving element 710 to translate the second portion 704.

The receiving element 710 may be formed with an open bottom portion, as in the illustrated embodiment, allowing the receiving element 710 and the second portion 704 to be separated from the straddle actuator 600 by moving the second portion 704 upwards from the straddle actuator 600. In other embodiments, a receiving element may be configured as a full nut, fully enclosing the straddle leadscrew 602. Some embodiments can include alternate straddle actuators. For example, some embodiments may include straddle actuators formed as a belt and pulley system, gear and gear rack system, chain and sprocket system, slider assembly (e.g., with detents), other system capable of transmitting a force from a straddle actuator to a receiving element in order to allow translation of a medical device or portion thereof, or combinations thereof.

The embodiment of the medical device 700 illustrated in FIG. 9 may include a tab 712. As shown, the tab 712 can extend through the straddle area (not shown; see straddle area 310 in FIG. 3) from an upper side to a lower side to secure the second portion 704 to the cross members 308 by biasing against the cross member 308 and/or by hooking around to prevent upward movement of the second portion 704 away from the cross member 308. The second portion 704 can include any number of tabs 712 (e.g., 1, 2, 3, 4, 5, 6, or more). For example, some embodiments may include a pair of oppositely disposed tabs, with each tab configured to bias against and/or hook around oppositely disposed cross members. Additionally, or alternatively, the medical device 700 can include one or more other linkage means, such as clips, hooks, clasps, and the like.

The embodiments of the present disclosure can be used in a variety of industrial applications. For example, some embodiments include a method of positioning a medical device using a stabilizing system according to the present disclosure, and such systems, devices, and methods can be used in a medical procedure where manipulation and positioning of a medical device is required and/or desired.

In addition, such systems, devices, and methods can be applied in a medical products testing industry or medical products analysis industry. For example, the ability of a medical device to be supported, positioned, reoriented, and/or manipulated can be tested and analyzed using the devices, systems, and methods of the present disclosure. Further, operational and durability limits of a medical device under such uses can be tested and/or analyzed.

In addition, embodiments of the present disclosure can be used in a medical operator training industry. For example, one or more devices, systems, or methods of the present disclosure can be used in a training application allowing a physician, surgeon, doctor, or medical engineer to undergo training by positioning, manipulating, reorienting, and/or repositioning a medical device.

The terms "approximately," "about," and "substantially" as used herein represent an amount or condition close to the stated amount or condition that still performs a desired function or achieves a desired result. For example, the terms "approximately," "about," and "substantially" may refer to an amount that deviates by less than 10%, or by less than 5%, or by less than 1%, or by less than 0.1%, or by less than 0.01% from a stated amount or condition.

In addition, unless expressly described otherwise, all stated amounts (e.g., angle measurements, dimension measurements, etc.) are to be interpreted as being "approximately," "about," and/or "substantially" the stated amount, regardless of whether the terms "approximately," "about," and/or "substantially" are expressly stated in relation to the stated amount(s).

Further, elements described in relation to any embodiment depicted and/or described herein may be combinable with elements described in relation to any other embodiment depicted and/or described herein. For example, any element described in relation to an embodiment depicted in FIGS. 1 through 6 may be combinable with an embodiment described in relation to an embodiment depicted in FIGS. 7 through 9.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A system, comprising:
    a medical device including a receiving element;
    a stabilizer body including a base and one or more support wings extending from the base, the medical device being supported by the one or more support wings and being translatable about at least one of the one or more support wings; and
    a straddle actuator coupled to the one or more support wings and configured to engage with the receiving element of the medical device;
    wherein actuation of the straddle actuator passes a force to the receiving element allowing at least a portion of the medical device to be translated relative to the stabilizer body.

2. The system of claim 1, wherein the straddle actuator comprises a threaded member and the receiver element comprises a complementary threaded portion.

3. The system of claim 2, wherein the complementary threaded portion is formed in a recessed portion of the receiver element.

4. The system of claim 1, wherein the stabilizer body includes one or more front support wings extending from a front portion of the base, and one or more rear support wings extending from a rear portion of the base.

5. The system of claim 4, wherein the one or more front support wings are configured to support a first portion of a medical device and the one or more rear support wings are configured to support a second portion of the medical device.

6. The system of claim 4, wherein the one or more front support wings include a support block, the support block being configured to frictionally prevent rotation or translation of the first portion of the medical device.

7. The system of claim 6, wherein the support block includes a notch and a support pin extending to the notch, the support pin being resiliently biased against the first portion of the medical device when positioned at the notch.

8. The system of claim 4, wherein the rear support wings form a straddle area, the straddle actuator being disposed within the straddle area and the straddle area being configured to receive a portion of the medical device and to allow the portion of the medical device to be translated within the straddle area upon actuation of the straddle actuator.

9. The system of claim 1, further comprising a platform and a translation actuator coupled to the platform.

10. The stabilizer system of claim 1, wherein actuation of the straddle actuator allows the second portion of the medical device to be translated relative to the first portion of the medical device and relative to the stabilizer body.

11. The stabilizer system of claim 1, wherein the straddle actuator includes a leadscrew, and wherein the at least a portion of the medical device is translated relative to the stabilizer body upon rotation of the leadscrew.

12. The stabilizer system of claim 1, further comprising a platform and a translation actuator coupled to the platform, the stabilizer body being positioned on the platform and including a receiving member configured to engage with the translation actuator, wherein actuation of the translation actuator passes a force to the receiving member allowing the stabilizer body to translate about the platform.

13. A method of positioning a medical device, the method comprising:
   positioning a medical device upon a stabilizer body to engage a threaded portion of a straddle actuator supported by a portion of the stabilizer body with a complementary threaded portion of the medical device, wherein
   the medical device includes a receiving element;
   the stabilizer body includes a base and one or more support wings extending from the base, the medical device being supported by the one or more support wings and being translatable about at least one of the one or more support wings; and
   a straddle actuator coupled to the one or more support wings and configured to engage with the receiving element of the medical device,
   wherein actuation of the straddle actuator passes a force to the receiving element allowing at least a portion of the medical device to be translated relative to the stabilizer body;
   translating the medical device relative to the stabilizer body by actuating the straddle actuator to move the complementary threaded portion along the threaded portion of the straddle actuator.

14. The method of claim 13, wherein the complementary threaded portion is formed within a recess of the receiving element of the medical device.

15. The method of claim 13, wherein the actuator comprises a fixed block separated from a gear box by a leadscrew having the threaded portion, wherein translating the medical device comprises moving the complementary threaded portion along the leadscrew.

16. The method of claim 13, further comprising translating the stabilizer body along a platform.

* * * * *